United States Patent
Song et al.

(10) Patent No.: US 11,352,317 B2
(45) Date of Patent: Jun. 7, 2022

(54) ROSIN-BASED SMALL MOLECULAR WEIGHT HYDROGELATOR AND ITS APPLICATION

(71) Applicant: Jiangnan University, Wuxi (CN)

(72) Inventors: Binglei Song, Wuxi (CN); Tingting Yan, Wuxi (CN); Danping Wang, Wuxi (CN); Zhenggang Cui, Wuxi (CN)

(73) Assignee: Jiangnan University, Wuxi (CN)

( * ) Notice: Subject to any disclaimer, the term of this patent is extended or adjusted under 35 U.S.C. 154(b) by 272 days.

(21) Appl. No.: 16/832,034

(22) Filed: Mar. 27, 2020

(65) Prior Publication Data

US 2020/0223789 A1 Jul. 16, 2020

Related U.S. Application Data

(63) Continuation of application No. PCT/CN2019/077616, filed on Mar. 11, 2019.

(30) Foreign Application Priority Data

Jan. 4, 2019 (CN) .......................... 201910007376.8
Jan. 23, 2019 (CN) .......................... 201910063397.1

(51) Int. Cl.
*C07C 237/48* (2006.01)
*A61L 26/00* (2006.01)
*C12N 5/00* (2006.01)
*C07C 231/14* (2006.01)
*B01F 17/00* (2006.01)
*C09K 23/00* (2022.01)

(52) U.S. Cl.
CPC .......... *C07C 237/48* (2013.01); *A61L 26/008* (2013.01); *C07C 231/14* (2013.01); *C09K 23/00* (2022.01); *C12N 5/0062* (2013.01); *C12N 5/0068* (2013.01); *C07C 2603/26* (2017.05); *C12N 2533/20* (2013.01); *C12N 2537/10* (2013.01)

(58) Field of Classification Search
CPC . C07C 237/48; C07C 231/14; C07C 2603/26; C09K 23/00; A61L 26/008; C12N 5/0062; C12N 5/0068; C12N 2533/20; C12N 2537/10; B01F 17/0042
USPC .......................................................... 514/788
See application file for complete search history.

(56) References Cited

FOREIGN PATENT DOCUMENTS

| CN | 103086927 A | 5/2013 |
|---|---|---|
| CN | 106140095 A | 11/2016 |
| CN | 107311261 A | 11/2017 |
| CN | 107311882 A | 11/2017 |
| CN | 108663836 A | 10/2018 |
| CN | 108837773 A | 11/2018 |

OTHER PUBLICATIONS

PCT/CN2019/077616 ISA210 Mail Date May 29, 2019.
PCT/CN2019/077616 ISA237 Mail Date May 29, 2019.
Ding Yq et. al. Synthesis and Physicochemical Properties of a Dehydroa -bietyl Amine Oxide Surfactant; Journal of Guangxi University for Nationalities; vol. 20, No. 2, Jun. 2014 p. 75.

*Primary Examiner* — Kristin A Vajda
(74) *Attorney, Agent, or Firm* — IPro, PLLC (57) ABSTRACT

The present disclosure discloses a rosin-based small molecular weight hydrogelator and an application thereof, and belongs to the fields of supramolecular chemistry, surfactant science and chemical utilization of rosin. The rosin-based small molecular hydrogel of the present disclosure can gel water at a very low concentration, and the critical gelling concentration is only 0.176 wt %. On average, each gelling agent molecule can hold 13,889 water molecules, which exhibits extremely high gel efficiency and the formed small molecular hydrogel also exhibits extremely high stability. This small molecule hydrogel is derived from the natural product rosin and has a mild nature. It can be used in the fields of drug sustained-release, tissue engineering, daily chemicals, medicine and so on. At the same time, the rosin-based small molecular hydrogel 6-dehydroabietylamide amine oxide in the present disclosure can form a stable gel emulsion for most oils, and can be used in many fields such as food, medicine, daily chemicals, tissue engineering, environmental protection, and water pollution control.

15 Claims, 8 Drawing Sheets

ROSIN-BASED SMALL MOLECULAR WEIGHT HYDROGELATOR AND ITS APPLICATION

TECHNICAL FIELD

The present disclosure relates to a rosin-based small molecular weight hydrogelator and its application, and belongs to the fields of supramolecular chemistry, surfactant science and chemical utilization of rosin.

BACKGROUND

Self-assembly of molecules is ubiquitous in nature and plays an important role in the origin and evolution of life. A hydrogel is a spatial network structure formed by colloidal particles by wrapping a large amount of water under certain conditions. As an important soft material, the hydrogel is widely present in nature and our daily life, and has important application in the fields of drug sustained release, tissue engineering, biological simulation and so on. With the development of supramolecular chemistry, the supramolecular hydrogel formed by small molecules through intermolecular forces (hydrophobic interaction, ionic interaction, hydrogen bond, host-guest interaction or pi-pi interaction and so on) has attracted widespread attention. The building block for constructing the supramolecular hydrogel is the the small molecular weight hydrogelator. Since molecular self-assembly is an extremely complex process, it is not yet possible to obtain a supramolecular hydrogel with specific functions by rationally designing the molecular structure, and thus the preparation of a supramolecular hydrogel system is a great challenge. It can be seen from the reported supramolecular hydrogel system that the weak interactions between the hydrophobic groups of suitably aligned molecules is an important driving force for self-assembly of molecules to form hydrogels.

The supramolecular hydrogel has wide application in the field of life science, so that the design and synthesis of the small molecule hydrogel by using a natural product as a main raw material are beneficial to constructing an environment-friendly and biocompatible supramolecular hydrogel system. Rosin is a renewable forest resource with rich yield. Products or deep-processed products of rosin have been widely used in various fields of industry and life, such as rubber, ink, coating, pesticide, medicine, food, electronics, and so on. Nevertheless, no example has been reported so far on rosin-based supramolecular hydrogel systems. If the rosin-based supramolecular hydrogel system can be obtained, the application of the natural product rosin and the research of the supramolecular hydrogel can be greatly expanded.

In addition, the gel emulsion refers to an emulsion system having a jelly-like appearance composed of a disperse phase (inner phase) and a continuous phase (outer phase) in the presence of a stabilizer. Due to special microstructure and properties, gel emulsions are widely used in the fields of food, cosmetics, materials, drug delivery, and so on. The type and concentration of the stabilizer has an important influence on the stability of the gel emulsion. Surfactants are the most commonly used stabilizers. In an oil-water system, surfactant molecules are directionally adsorbed at an oil-water interface to reduce the interface energy, and the formation of gel emulsion is promoted. However, in order to achieve the viscoelasticity of a gel, the amount of surfactant used during the preparation of the gel emulsion is extremely large, typically 5 to 30% of the continuous phase, and the gel can only be formed after the volume fraction of the disperse phase is greater than 74%. These requirements severely limit the practical application of gel emulsions.

The small molecular weight hydrogelator forms a fiber network structure through self-assembly of molecules involving various molecular interactions such as hydrogen bond, pi-pi stacking, van der Waals force, electrastatic interaction and host-guest interaction, which can enable a solvent to lose fluidity. If small molecular weight hydrogelators are used as a new class of stabilizers, the resulting gel emulsion system will be different from conventional gel emulsion systems. The gel emulsion using the small molecular weight hydrogelator as the stabilizer has a continuous phase in a gel state and a disperse phase physically wrapped in a gel network; and such gel emulsion system is not limited by the condition that the continuous phase is more than 74%, so that the volume fraction of the disperse phase in the emulsion can be greatly widened. However, not all small molecular weight hydrogelator can stabilize gel emulsions. The aggregation structure formed by the small molecular weight hydrogelator shall be able to resist the corrosion of the organic oil phase and have the effect of reducing the interfacial tension. Therefore, how to design and synthesize the novel small molecular weight hydrogelator as desired to prepare the novel gel emulsion system is currently the key and difficult point concerned in the field of colloid chemistry.

SUMMARY

In order to solve the above problems, the abietic acid is introduced into the structure of the small molecular weight hydrogelator, and thus a rosin-based supramolecular hydrogel system which has good biocompatibility and degradability and meets the green chemistry requirements is obtained. The application range of natural product rosin and the research range of supramolecular hydrogel are greatly expanded. Since the main part of the abietic acid is a rigid hydrophobic group with a tricyclic diterpene structure and has a stable spatial configuration, the small molecular weight hydrogelator thus has an extremely high gel efficiency.

The present disclosure provides a small molecular weight hydrogelator 6-dehydroabietylamide-N,N-dimethyl-hexylamine oxide (R-6-OA) meeting the green chemical requirements by taking dehydroabietic acid as as a raw material, followed by a series of reactions. Furthermore, the supramolecular hydrogel system is prepared by taking the molecular weight hydrogelator as a building block, which is beneficial for the application of rosin in the field of supramolecular chemistry.

Further, a class of O/W type gel emulsion can be prepared by taking the 6-dehydroabietylamide-N,N-dimethyl-hexylamine oxide of the present disclosure as a stabilizer. The 6-dehydroabietylamide-N,N-dimethyl-hexylamine oxide prevents droplet aggregation by the three-dimensional network structure formed in the continuous phase while reducing oil-water interfacial tension. In such gel emulsions, the volume fraction of the disperse phase is extremely wide and can be arbitrarily adjusted between 1% and 98% (v/v), breaking the restriction that the volume of the disperse phase of the conventional gel emulsion must be greater than 74%. At the same time, it is possible to prepare a stable gel emulsion with many oils, which greatly broadens the application range of the gel emulsion.

A first object of the present disclosure is to provide a compound having the formula (1):

Formula (1)

A second object of the present disclosure is to provide a method for the preparation of the compound comprising: synthesizing 6-dehydroabietylamide-N,N-dimethyl-hexylamine oxide by taking dehydroabietic acid being the main component in disproportionated rosin as a raw material.

In one embodiment, the synthetic route of the compound (6-dehydroabietylamide-N,N-dimethyl-hexylamine oxide) is as follows:

In one embodiment, the steps of synthesizing the compound comprise:

(1) reacting dehydroabietic acid with thionyl chloride under the catalysis of 4-dimethylaminopyridine to obtain a crude product of dehydroabietyl chloride;

(2) reacting dehydroabietyl chloride with 1,6-hexanediamine;

(3) dissolving the product obtained in the previous step and then reacting with the formic acid and formaldehyde added dropwise;

(4) reacting the compound obtained in the previous step with $H_2O_2$ under the catalysis of the catalysts citric acid and disodium edetate to obtain 6-dehydroabietylamide-N,N-dimethyl-hexylamine oxide.

In one embodiment, the specific steps of synthesizing the compound are as follows:

Synthesis of Compound 1: The dehydroabietic acid solid is added to a three-necked flask with a reflux condenser, and a catalytic amount of 4-dimethylaminopyridine is added thereto, and the exhaust gas during the reaction is absorbed by the alkali solution. When the temperature is raised to 50° C., thionyl chloride is slowly added dropwise, and a large amount of gas is generated. After completion of the dropwise addition of thionyl chloride, the reaction is carried out at 72° C. for 3 h. After completion of the reaction, the cooled reaction product is subjected to distillation under reduced pressure to remove excess thionyl chloride to obtain a crude Compound 1.

Synthesis of Compound 2: A certain amount of 1,6-hexanediamine and dichloromethane are added to a three-necked flask with sufficient stirring. When the temperature is below −20° C., the solution of Compound 1 in dichloromethane is slowly added dropwise, and the reaction is continued for 3 h after completion of the dropwise addition. Water is added to the mixture, and the mixture is extracted with dichloromethane. The organic layer is washed with water for 5-6 times, and then the organic layer is dried by anhydrous sodium sulfate, and the solvent remaining in the extract is removed by distillation under reduced pressure to obtain a yellow viscous liquid containing Compound 2.

Synthesis of Compound 3: The mixture containing Compound 2 is dissolved in ethanol. Formic acid solution and formaldehyde solution are slowly added dropwise at room temperature in sequence. After that, the reaction is carried out at 80° C. for 8 h. After completion of the reaction, the product is adjusted to pH 11 with a 15% NaOH solution, and extracted with diethyl ether. The extract is dried with anhydrous sodium sulfate, and the solvent is removed under reduced pressure to obtain a yellow viscous liquid containing Compound 3.

Synthesis of Compound 4: Compound 3 is dissolved in ethanol, and a catalytic amount of citric acid and disodium edetate were added. When the temperature is raised to 55° C., 30% $H_2O_2$ is slowly added dropwise. After completion of the dropwise addition, the reaction is carried out at 80° C. for 5 h. After completion of the reaction, ethanol is removed by distillation under reduced pressure. The product is purified by silica gel column chromatography (eluent:ethyl acetate:methanol=4:1) to obtain Compound 4 as a white powdery solid after vacuum drying.

A third object of the present disclosure is to provide a supramolecular hydrogel comprising taking the 6-dehydroabietylamide-N,N-dimethyl-hexylamine oxide of the present disclosure as a gelator.

In one embodiment, the supramolecular hydrogel is formed by dissolving 6-dehydroabietylamide-N,N-dimethyl-hexylamine oxide into water.

In one embodiment, the supramolecular hydrogel is formed at a temperature below 40° C.

In one embodiment, the concentration of 6-dehydroabietylamide-N,N-dimethyl-hexylamine oxide in the supramolecular hydrogel ranges from 3 mmol·L$^{-1}$ to 1,000 mmol·L$^{-1}$.

A third object of the present disclosure is to provide a sustained-release material prepared from the 6-dehydroabietylamide-N,N-dimethyl-hexylamine oxide of the present disclosure and a substance requiring a sustained-release.

In one embodiment, the substance requiring a sustained-release is a functional component including: a drug or a nutritional ingredient.

In one embodiment, the sustained-release material is obtained by dispersing a substance requiring a sustained-release in water, and then forming a hydrogel by taking 6-dehydroabietylamide-N,N-dimethyl-hexyl amine oxide as a gelator.

A fourth object of the present disclosure is to provide a pharmaceutical wound dressing in which a hydrogel is formed by taking the 6-dehydroabietylamide-N,N-dimethyl-hexylamine oxide of the present disclosure as a gelator and contains anti-inflammatory or anti-bacterial ingredients.

A fifth object of the present disclosure is to provide a water-soil moisturizing agent comprising the use of the 6-dehydroabietylamide-N,N-dimethyl-hexylamine oxide of the present disclosure. The water-soil moisturizing agent can absorb and slowly release a large amount of water, which has a moisturizing and drought-resistant effect.

A sixth object of the present disclosure is to provide a hydrogel mask in which a hydrogel is formed by taking the 6-dehydroabietylamide-N,N-dimethyl-hexylamine oxide of the present disclosure as a main gelling agent. Optionally, one or more of collagen, hyaluronic acid, arbutin, nicotinamide are also injected into the mask.

A seventh object of the present disclosure is to provide a method for cell incubation comprising a hydrogel by taking the 6-dehydroabietylamide-N,N-dimethyl-hexylamine oxide of the present disclosure as a gelator to provide a three-dimensional environment for cell growth.

The present disclosure also provides the use of the 6-dehydroabietylamide-N,N-dimethyl-hexylamine oxide in the fields of drug sustained release, tissue engineering, cell incubation, sewage treatment, home care product and so on.

An eighth object of the present disclosure is to provide an O/W type gel emulsion, and the stabilizer of the O/W type gel emulsion comprises 6-dehydroabietylamide-N,N-dimethyl-hexylamine oxide (R-6-OA) having the following molecular structure:

In one embodiment, the concentration of 6-dehydroabietylamide-N,N-dimethyl-hexylamine oxide in the gel emulsion ranges from 0.22% to 80% of the mass of the continuous phase, and the volume fraction of the disperse phase ranges from 1% to 98%. Optionally, the O/W type gel emulsion system consists of an aqueous phase, an oil phase, and a rosin-based amine oxide surfactant 6-dehydroabietylamide-N,N-dimethyl-hexylamine oxide. Optionally, the preparation of the O/W type gel emulsion can be formed by a homogenizer or by hand shaking; specifically, the O/W type gel emulsion can be formed by dissolving the 6-dehydroabietylamide-N,N-dimethyl-hexylamine oxide in water, then adding the oil phase and carrying out a homogenization or a hand shaking. Optionally, the oil phase may be an aliphatic hydrocarbon mineral oil, a triglyceride or an edible oil; in particular, the O/W type gel emulsion is prepared by dissolving the 6-dehydroabietylamide-N,N-dimethyl-hexylamine oxide in water by heating, adding the oil phase in a suitable proportion, homogenizing, thoroughly mixing the oil phase and water phase to form an emulsion, and then cooling to obtain a gel emulsion.

A ninth object of the present disclosure is to provide the application of the gel emulsion. Optionally, the application includes the application in the fields of food, cosmetic, material, drug delivery, etc.

Optionally, the application in the food field can include imitating the texture characteristics of saturated fatty acids to design low-fat foods and serving as a delivery system for functional factors to embed probiotics, flavor substances and so on. Gel emulsion can be used as a fat substitute to effectively reduce the content of saturated fatty acids and increase the content of polyunsaturated fatty acids, essential amino acids, minerals and so on. A gel emulsion is prepared by taking the gel formed by 6-dehydroabietylamide-N,N-dimethyl-hexylamine oxide as a continuous phase and taking sunflower seed oil as a disperse phase, and can be used as a substitute for pig fat to reduce the content of saturated fatty acids in the fresh meat product.

Optionally, the application in the cosmetic field specifically comprises: preparing a smear-type mask by adding a moisturizing ingredient to the gel emulsion to improve the water-locking function without a greasy feeling; adding the active substance to the inner phase to delay the release rate of the active ingredient by releasing at two-phase interface, prolong the action time of the active ingredient, and thus achieve the effects of controlled release and delayed release.

Optionally, the application in the material field is for the synthesis of porous materials.

Optionally, the application in the drug delivery field specifically comprises: embedding a drug molecule in a gel emulsion system to improve the stability of the drug molecule and achieve the purpose of slow release of the drug molecule.

A tenth object of the present disclosure is to provide a method for transporting an oil by adding 6-dehydroabietylamide-N,N-dimethyl-hexylamine oxide as a stabilizer to the oil to obtain a solid or semi-solid oil for transportation.

Optionally, the method for transporting an oil further comprises carrying out an external stimulation to demulsify after transportation. Optionally, the external stimuli comprises adding an external stimuli, such as an alcohol including methanol or ethanol, and destroying the gel structure of the 6-dehydroabietylamide-N,N-dimethyl-hexylamine oxide in the continuous phase, At the same time, the addition of alcohol reduces the stability of the adsorption film formed by the 6-dehydroabietylamide-N,N-dimethyl-hexylamine oxide molecule at the oil-water interface, which leads to the demulsification of the emulsion. Optionally, the external stimuli may also be heating, such as heating to above 40° C. After heating, the gel state of the continuous phase is first broken, so that the gel emulsion becomes a fluid emulsion, and the heating is continued to increase the Brownian motion of the oil droplets, causing flocculation and coalescence of the dispersed phase, which leads to the demulsification of the gel emulsion.

An eleventh object of the present disclosure is to provide a method for synthesizing a porous material, which comprises: adding a crosslinking agent and an initiator to an aqueous phase, preparing an emulsion of 6-dehydroabietylamide-N,N-dimethyl-hexylamine oxide upon heating, adding a reducing agent to the prepared emulsion, stirring uniformly, transferring the emulsion to a mold and cooling down to form a gel emulsion, curing, washing the cured monolith to remove the gel emulsion and then drying under vacuum. Since the oil-water volume ratio of the gel emulsion stabilized by 6-dehydroabietylamide-N,N-dimethyl-hexylamine oxide can be arbitrarily regulated, the porous material prepared by taking the gel emulsion stabilized by 6-dehydroabietylamide-N,N-dimethyl-hexylamine oxide as a template can be arbitrarily adjusted in pore size.

A twelfth object of the present disclosure is to provide a functional component delivery system comprising preparing an O/W type gel emulsion by using 6-dehydroabietylamide-N,N-dimethyl-hexylamine oxide, and the functional component is embedded in a gel emulsion. Optionally, the functional component s include, but are not limited to, probiotics, flavor substances, nutrients and drugs.

Advantageous Effects of the Present Disclosure

A rosin-based small molecule 6-dehydroabietylamide-N,N-dimethyl-hexylamine oxide meeting the "green chemistry" requirement can be obtained from the rosin derivative dehydroabietic acid via simple synthesis steps. 6-dehydroabietylamide-N,N-dimethyl-hexylamine oxide can form a left-handed helical fiber structure with a cross-sectional diameter of about 10 nm by molecular self-assembly and gel water at normal temperature, and the critical gelling concentration of 6-dehydroabietylamide-N,N-dimethyl-hexylamine oxide is only 0.176%. On average, each gelling agent molecule can immobilize 13,889 water molecules, which has extremely high gelling efficiency. This small molecular hydrogel is derived from the natural product rosin and has a mild and non-toxic nature. The hydrogel has important applications in the fields of drug release, tissue engineering, cell incubation, sewage treatment, home care products and so on.

The 6-dehydroabietylamide-N,N-dimethyl-hexylamine oxide of the present disclosure can be used for preparing an O/W type gel emulsion product, and has the advantages of simple process, good emulsion stability, environmental friendliness and economy. Compared with the traditional surfactant-stabilized gel emulsion system, the amount of surfactant 6-dehydroabietylamide amine oxide required for this type of O/W type gel emulsion is much lower than that of traditional surfactants, in which the lowest amount is only 0.22% of the mass of the continuous phase. At the same time, the volume fraction of the dispersed phase can be freely adjusted between 1% and 98% (v/v), breaking the restriction that the volume ratio of the continuous phase in the conventional gel emulsion must be greater than 74%, greatly expanding the type and application range of the gel emulsion. Most of the oil can form a stable gel emulsion by utilizing the rosin-based surfactant 6-dehydroabietylamide-N,N-dimethyl-hexylamine oxide in the present disclosure as a stabilizer. It can be seen that the present disclosure has a broad application prospect and an important application value.

DETAILED DESCRIPTION

The synthetic route of 6-dehydroabietylamide-N,N-dimethyl-hexylamine oxide is as follows:

EXAMPLE 1: SYNTHESIS OF COMPOUND 1

The dehydroabietic acid solid (30 g, 0.1 mol) was added to a three-necked flask equipped with an exhaust gas absorption device and a reflux condenser, and a small amount of 4-dimethylaminopyridine (DMAP) was added as a catalyst. When the temperature was raised to 50° C., thionyl chloride (17.94 g, 0.15 mol) was slowly added dropwise. A large amount of acid gas was generated during this process, which was absorbed by the exhaust gas absorption device. After completion of the dropwise addition, the temperature was set to 72° C. and the reaction was continued for 3 h. After completion of the reaction, excess thionyl chloride was removed by rotary distillation under reduced pressure to obtain a crude Compound 1.

EXAMPLE 2: SYNTHESIS OF COMPOUND 2

In a three-necked flask, 1,6-hexanediamine (58.1 g, 0.5 mol) and dichloromethane were added and stirred well. At a temperature of −20° C., a solution of dehydroabietyl chloride (0.1 mol) in dichloromethane was slowly added dropwise, and the reaction was continued for 3 h after completion of the dropwise addition. After that, the product was transferred to a 1,000 mL beaker, water was added to the mixture, and the mixture was extracted with dichloromethane. The obtained organic layer was washed with water for 5-6 times and then the organic layer was dried over anhydrous sodium sulfate, and the solvent was removed under reduced pressure to obtain Compound 2 as a yellow viscous liquid.

EXAMPLE 3: SYNTHESIS OF COMPOUND 3

Compound 2 was dissolved in ethanol, and an 88% formic acid (26.15 g, 0.5 mol) solution and a 30% formaldehyde (50.03 g, 0.5 mol) solution were slowly added dropwise at room temperature in sequence. After completion of the dropwise addition, the reaction was carried out at 80° C. for 8 h. After completion of the reaction, the product was adjusted to pH=11 with a 15% NaOH solution and extracted with diethyl ether. The organic layer was dried over anhydrous sodium sulfate, and the solvent was removed under reduced pressure to obtain Compound 3 as a yellow viscous liquid.

EXAMPLE 4: SYNTHESIS OF COMPOUND 4

Compound 3 was dissolved in ethanol, and a small amount of citric acid and disodium edetate were added. When the temperature was raised to 55° C., 30% $H_2O_2$ (17 g, 0.15 mol) was slowly added dropwise, and after completion of the dropwise addition, the reaction was carried out at 80° C. for 5 h. After completion of the reaction, ethanol was removed by distillation under reduced pressure. The product was purified by silica gel column chromatography (eluent: ethyl acetate:methanol=4:1) to obtain Compound 4 as a white powdery solid after vacuum drying.

EXAMPLE 5: SYNTHESIS OF 2-dehydroabietylamide-N,N-dimethyl-ethylamine oxide and 3-dehydroabietylamide-N,N-dimethyl-propylamine oxide Compound 1 was reacted with N,N-dimethylethylenediamine and N,N-dimethylpropanediamine, respectively, and then subjected to $H_2O_2$ oxidation and column chromatography to obtain two comparative 2-dehydroabietylamide-N,N-dimethyl-ethylamine oxide and 3-dehydroabietylamide-N,N-dimethyl-propylamine oxide respectively. Both are white powdery solids after drying.

EXAMPLE 6: DETERMINATION OF MOLECULAR STRUCTURE AND PURITY OF 6-dehydroabietylamide-N,N-dimethyl-hexylamine oxide An appropriate amount of rosin-based small molecular weight hydrogelator 6-dehydroabietylamide-N,N-dimethyl-hexylamine oxide was weighed and dissolved in deuterated reagent DMSO. The $^1H$ NMR test was carried out at 25° C. using an Aduance III NMR spectrometer. The resonant frequency of $^1H$ is 400 MHz. It can be seen from the hydrogen nuclear magnetic resonance spectrum of 6-dehydroabietylamide-N,N-dimethyl-hexylamine oxide in FIG. 4 that chemical shift of each hydrogen was consistent with the target product 6-dehydroabietylamide-N,N-dimethyl-hexylamine oxide, indicating that the final product was obtained. At the same time, there are no impurity peaks at the spectrum, indicating a high purity of the product.

Figure 1:
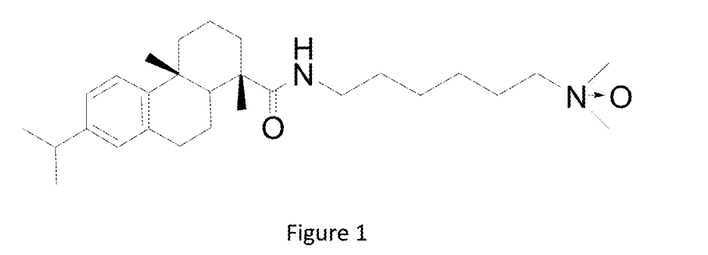
FIG. 1 is the molecular structure of 6-dehydroabietylamide-N,N-dimethyl-hexylamine oxide.
Figure 2:
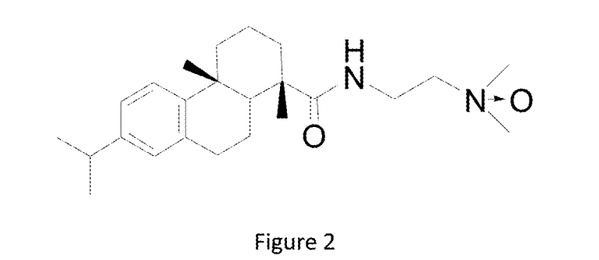
FIG. 2 is the molecular structure of 2-dehydroabietylamide-N,N-dimethyl-ethylamine oxide.
Figure 3:
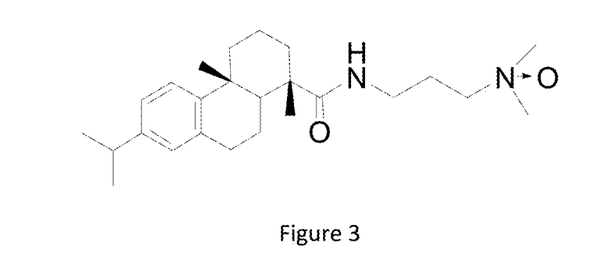
FIG. 3 is the molecular structure of 3-dehydroabietylamide-N,N-dimethyl-propylamine oxide.
Figure 4:
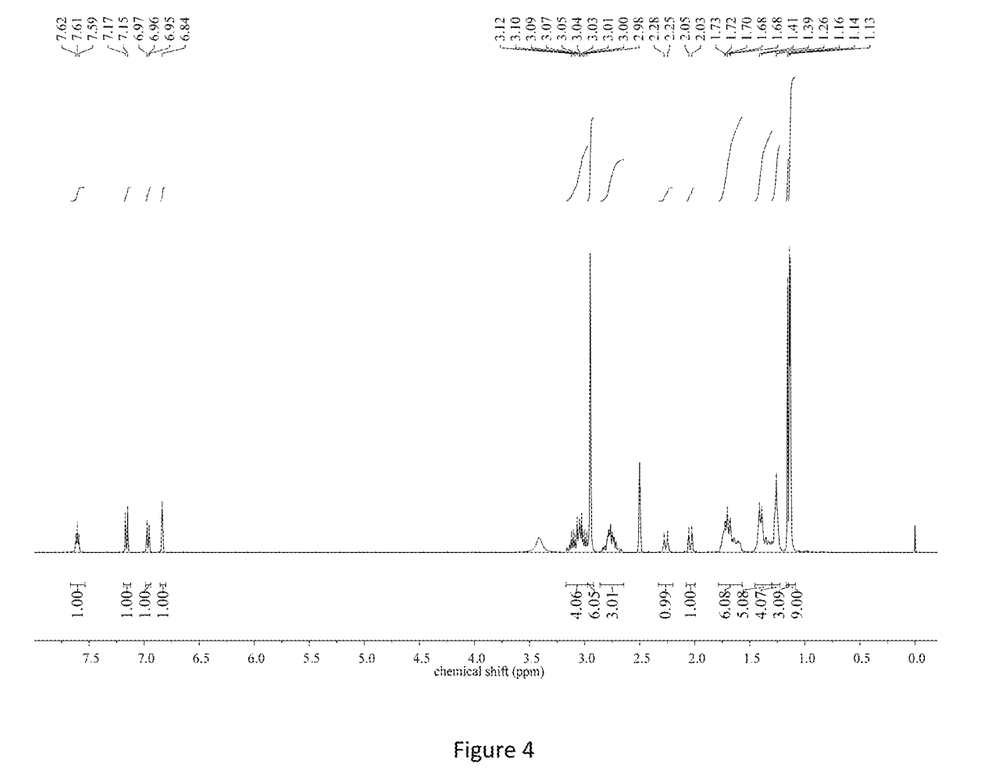
FIG. 4 is a hydrogen nuclear magnetic resonance spectrum of 6-dehydroabietylamide-N,N-dimethyl-hexylamine oxide.

1H NMR (400 MHz, DMSO) δ 7.61 (t, 1H, N20-1H), 7.16 (d, 1H, C11-1H), 7.03-6.92 (d, 1H C14-1H), 6.84 (s, 1H, C12-1H), 3.17-2.97 (m, 4H, C26-2H, C21-2H), 2.95 (s, 6H, C27-3H, C28-3H), 2.85-2.64 (m, 3H, C8-2H, C15-1H), 2.26 (d, 1H, C4-1H), 2.04 (d, 1H, C6-1H), 1.77-1.57 (m, 6H, C25-2H, C22-2H, C2-1H, C7-1H), 1.40 (m, 5H, C3-2H,

C7-1H, C2-1H, C4-1H), 1.26 (m, 4H, C23-2H, C24-2H), 1.16 (s, 3H, C18-3H), 1.14 (d, 9H, C16-3H, C17-3H, C19-3H).

EXAMPLE 7: DETERMINATION OF GEL BEHAVIOR

To 1 mL of deionized water, 6-dehydroabietylamide-N,N-dimethyl-hexylamine oxide was added (concentrations were 4 mmol·L$^{-1}$, 10 mmol·L$^{-1}$, 15 mmol·L$^{-1}$, 20 mmol·L$^{-1}$, and 25 mmol·L$^{-1}$, respectively). The solution was heated to 40° C. to completely dissolve the 6-dehydroabietylamide-N,N-dimethyl-hexylamine oxide, and then allowed to stand at room temperature, and the solution state was investigated.

Figure 5:
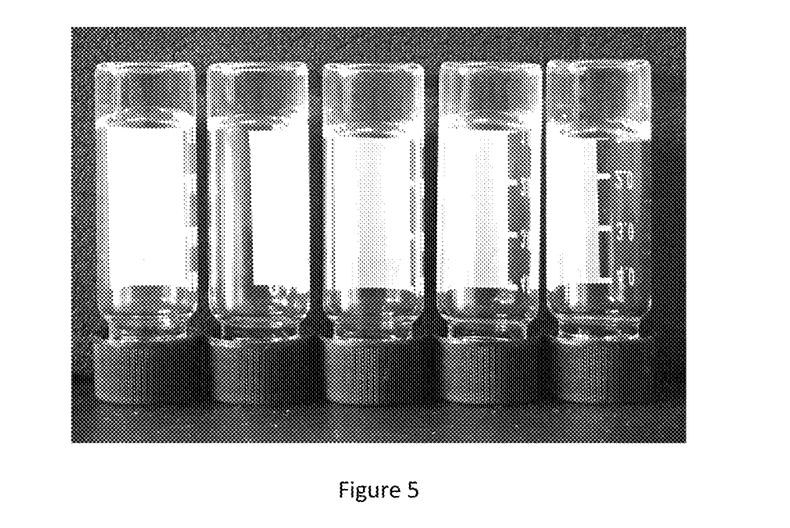
FIG. 5 is a photograph of the appearance of a gel formed by 6-dehydroabietylamide-N,N-dimethyl-hexylamine oxide (concentrations from left to right are 4 mmol·L$^{-1}$, 10 mmol·L$^{-1}$, 15 mmol·L$^{-1}$, 20 mmol·L$^{-1}$, and 25 mmol·L$^{-1}$, respectively).

It can be seen from the photograph of the appearance of a gel formed by 6-dehydroabietylamide-N,N-dimethyl-hexylamine oxide in FIG. 5 (concentrations from left to right were 4 mmol·L$^{-1}$, 10 mmol·L$^{-1}$, 15 mmol·L$^{-1}$, 20 mmol·L$^{-1}$, and 25 mmol·L$^{-1}$, respectively) that when the concentration of 6-dehydroabietylamide-N,N-dimethyl-hexylamine oxide was greater than 4 mmol·L$^{-1}$, the 6-dehydroabietylamide-N,N-dimethyl-hexylamine oxide can support its own weight without flowing after invertion, indicating the formed gel has excellent viscoelasticity.

In a hydrogel formed by 4 mmol·L$^{-1}$ of 6-dehydroabietylamide-N,N-dimethyl-hexylamine oxide, the critical gelling concentration of the 6-dehydroabietylamide-N,N-dimethyl-hexylamine oxide was only 0.176%. Upon conversion, on average, each gelling agent molecule can immobilize 13,889 water molecules, showing extremely high gelling efficiency.

Figure 6:
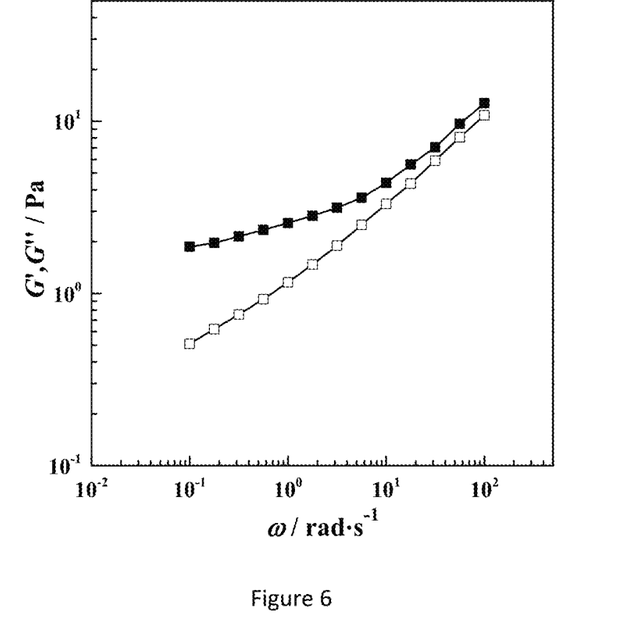
FIG. 6 is a dynamic shear diagram of a gel formed by 5 mmol·L$^{-1}$ 6-dehydroabietylamide-N,N-dimethyl-hexylamine oxide (G is the storage modulus with a solid symbol; G" is the loss modulus with a hollow symbol).

EXAMPLE 8: VISCOELASTICITY INVESTIGATION OF HYDROGELS FORMED BY 6-dehydroabietylamide-N,N-dimethyl-hexylamine oxide The gel with a 6-dehydroabietylamide-N,N-dimethyl-hexylamine oxide concentration of 5 mmol·L$^{-1}$ was first heated to 45° C. and then cooled to 25° C. After completely gelling, the samples were tested for rheological properties at 25° C. Prior to dynamic scanning, a stress scan was performed to determine the linear viscoelastic region of the sample, and the samples are investigated in a linear viscoelastic region. It can be seen from the dynamic shear diagram of the gel formed by 5 mmol·L$^{-1}$ 6-dehydroabietylamide-N,N-dimethyl-hexylamine oxide in FIG. 6 that within the tested frequency range, the elastic modulus of the gel formed by 6-dehydroabietylamide-N,N-dimethyl-hexylamine oxide was always greater than the viscous modulus, indicating that the gel system shows excellent elasticity. Within the tested frequency range of 0.01-100 rad·s$^{-1}$, the corresponding elastic modulus of the gel was measured as 10.8 Pa-12.7 Pa, and the viscous modulus of the gel was measured as 0.5 Pa-1.85 Pa. It can be seen that the elastic modulus of the sample was always greater than the viscous modulus, exhibiting prominent elastic properties.

Figure 7:
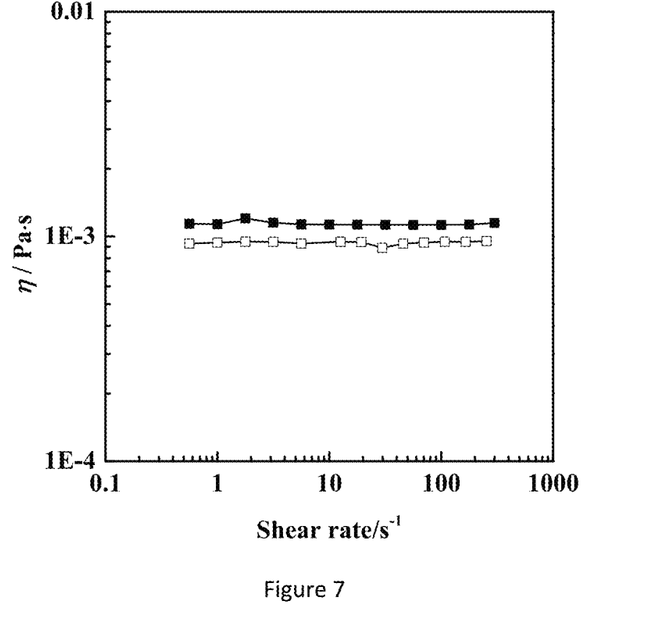
FIG. 7 is a steady-state shear diagram of 5 mmol·L$^{-1}$ 2-dehydroabietylamide-N,N-dimethyl-ethylamine oxide aqueous solution (solid symbol) and 3-dehydroabietylamide-N,N-dimethyl-propylamine oxide aqueous solution (hollow symbol).

EXAMPLE 9: VISCOELASTIC MEASUREMENT OF COMPARATIVE 2-dehydroabietylamide-N,N-dimethyl-ethylamine oxide AND 3-dehydroabietylamide-N,N-dimethyl-propylamine oxide AQUEOUS SOLUTIONS It can be seen from the steady-state shear diagram of oth at 5 mmol·L$^{-1}$ in FIG. 7 that whether at high shear rates or low shear rates, the viscosity of the system was comparable to the viscosity of water, and always behaved as a Newtonian fluid. Thus, neither 2-dehydroabietylamide-N,N-dimethyl-ethylamine oxide nor 3-dehydroabietylamide-N,N-dimethyl-propylamine oxide could form a gel.

Figure 8:
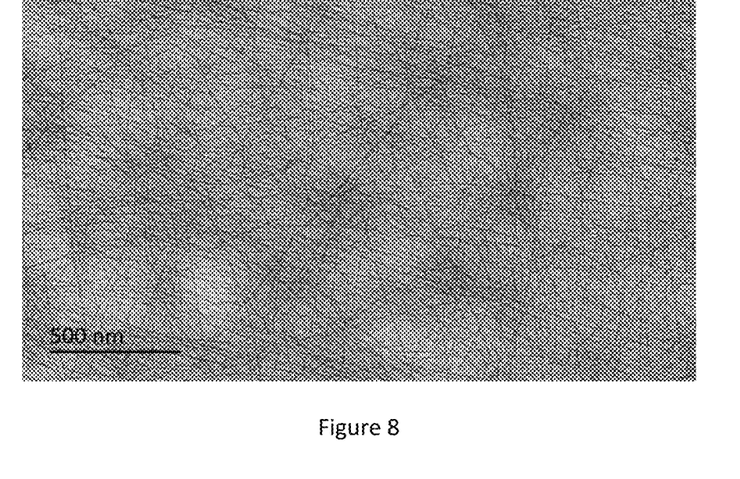
FIG. 8 is an in situ frozen transmission electron micrograph of a 5 mmol·L$^{-1}$ 6-dehydroabietylamide-N,N-dimethyl-hexylamine oxide gel.

EXAMPLE 10: MEASUREMENT OF MICROSTRUCTURE OF THE GEL SYSTEM FORMED BY 6-dehydroabietylamide-N,N-dimethyl-hexylamine oxide Sample preparation was carried out using an environment controlled low temperature sample preparation device Cryoplunge TM3, and the ambient temperature was fixed at 25° C. The relative humidity in the device cavity was adjusted to over 90%, about 5 μL of the sample was pipetted onto the surface of the micro-grid, and the droplets on the surface of the micro-gate were absorbed by patting the sample with the filter paper on both sides of Cp3 to obtain a very thin liquid film. The sample was then quickly inserted into liquid ethane cooled liquid nitrogen. The frozen sample was transferred to a sample rod cooled with liquid nitrogen and transferred to a transmission electron microscope for observation at an operating voltage of 120 kV. It can be seen from the in situ frozen transmission electron micrograph of a hydrogel sample formed by 5 mmol·L$^{-1}$ 6-dehydroabietylamide-N,N-dimethyl-hexylamine oxide in FIG. 8 that the microscopic morphology of the hydrogel was a relatively rigid nanofiber having a cross-sectional diameter of about 10 nm and a length of more than 2 μm.

The 6-dehydroabietylamide-N,N-dimethyl-hexylamine oxide hydrogel also exhibited an extremely strong stability. The reason was that the 6-dehydroabietylamide-N,N-dimethyl-hexylamine oxide molecule formed a left-handed helical fiber structure having a diameter of about 10 nm by molecular self-assembly. The fibers were intertwined to form a three-dimensional network structure, and then the water molecules are fixed by capillary action and, surface tension, leading to the formation of a stable hydrogel.

Figure 9:
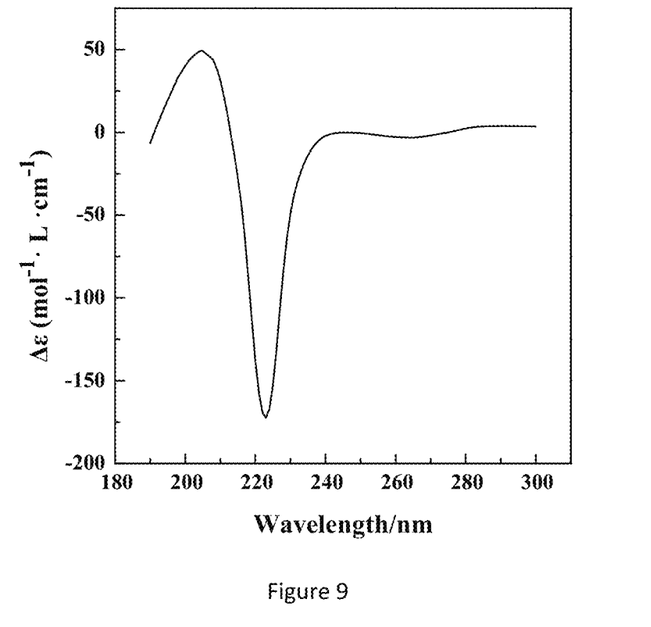
FIG. 9 is a circular dichroism spectrum of a 5 mmol·L$^{-1}$ 6-dehydroabietylamide-N,N-dimethyl-hexylamine oxide gel.

EXAMPLE 11: MEASUREMENT OF A CIRCULAR DICHROISM SPECTRUM OF A GEL FORMED BY 5 MMOL·L$^{-1}$ 6-dehydroabietylamide-N,N-dimethyl-hexylamine oxide The measurement was carried out on a circular dichroism spectrometer model MOS-450. The signal was recorded at intervals of 0.1 nm within the wavelength range of 300-180 nm. Gel samples were measured using a 0.1 mm quartz sample cell. It can be seen from the circular dichroism spectrum of the 5 mmol·L$^{-1}$ 6-dehydroabietylamide-N,N-dimethyl-hexylamine oxide gel in FIG. 9 that the gel sample exhibited a strong CD signal, exhibited a positive absorption peak in the wavelength range of 190-212 nm, and exhibited a negative absorption peak in the wavelength range of 212-300 nm, indicating that the nanofiber formed in the system was a chiral aggregate structure having a left-handed helix.

EXAMPLE 12: GEL SUSTAINED-RELEASE PERFORMANCE TEST

Rhodamine B was embedded in a hydrogel formed by 20 mmol·L$^{-1}$ 6-dehydroabietylamide-N,N-dimethyl-hexylamine oxide and in vitro release experiments were carried out in a constant temperature oscillating water bath at 37° C.

Figure 10:
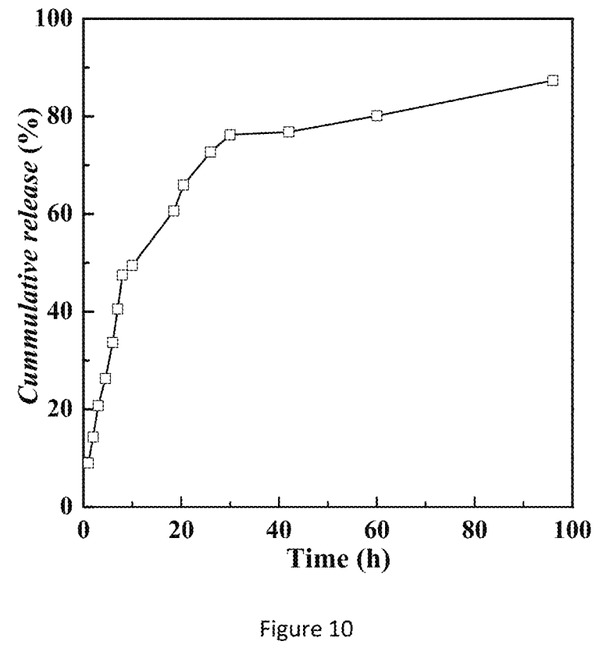
FIG. 10 is a release curve of Rhodamine B embedded by 20 mmol·L$^{-1}$R-6-OA at 37° C.

The absorbance of the release solution was measured by an ultraviolet-visible spectrophotometer to obtain an in vitro release curve. It can be seen from FIG. 10 that the release rate of Rhodamine B was only 28% within 5 h, and the release rate of Rhodamine B was 76% in 40 h, after which Rhodamine B exhibited a slower release. It can be seen that the hydrogel formed by 6-dehydroabietylamide-N,N-dimethyl-hexylamine oxide had good sustained-release ability and can be used in the fields of drug sustained release and so on.

Figure 11:
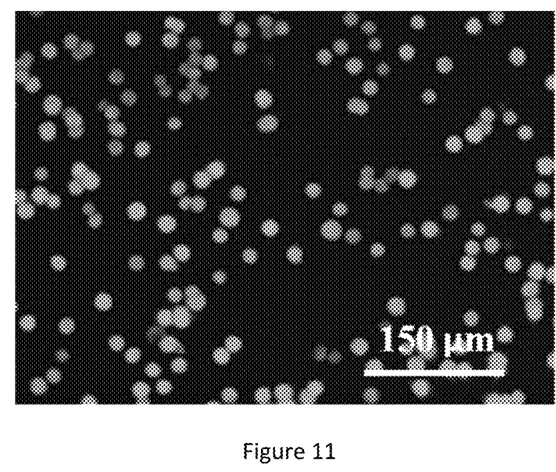
FIG. 11 is a laser confocal micrograph of L929 cells after incubation.

EXAMPLE 13: USE OF HYDROGEL FORMED BY 6-dehydroabietylamide-N,N-dimethyl-hexylamine oxide FOR CELL INCUBATION L929 cells were encapsulated in a 6-dehydroabietylamide-N,N-dimethyl-hexylamine oxide gel under sterile conditions for 3D cell incubation. The cell suspension was added into the 6-dehydroabietylamide-N,N-dimethyl-hexylamine oxide solution with a sol state, and a cell/hydrogel system was formed within 30 s, and further incubated at 37° C. for 15 min. Thereafter, 2 mL of RPMI-1640 medium containing 10% FBS fetal bovine serum and 1% penicillin/streptomycin was gently added to the incubation dish, and the cell/hydrogel system was incubated in a humidified atmosphere of 37° C. and 5% $CO_2$. The medium was replaced after 1 h of incubation and then replaced every 12 h. After incubation for 24 h, 48 h and 96 h, the cell/hydrogel system was stained with FDA/PI and the cells were observed by a confocal laser scanning microscope. It can be seen from FIG. 11 that L929 cells had higher viability and proliferative ability in the gel due to excellent biocompatibility of the 6-dehydroabietylamide-N,N-dimethyl-hexylamine oxide hydrogel. It can be seen that 6-dehydroabietylamide-N,N-dimethyl-hexylamine oxide hydrogel can be used as a 3D cell incubation scaffold and had potential application in cell therapy and tissue regeneration.

EXAMPLE 14

Determination of surface tension. A series of aqueous surfactant solutions having different concentrations were prepared, and the surface tension was measured by a ring method at 25° C., and the surface tension curve was plotted.

Figure 12:
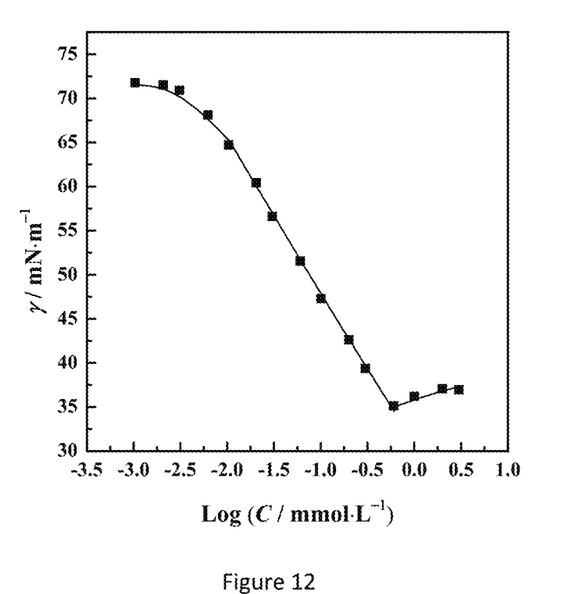
FIG. 12 is a diagram showing the surface tension γ of the 6-dehydroabietylamide-N,N-dimethyl-hexylamine oxide as a function of the concentration C.

It can be seen from the surface tension y of the 6-dehydroabietylamide-N,N-dimethyl-hexylamine oxide as a function of the concentration C in FIG. 12 that the surfactant 6-dehydroabietylamide-N,N-dimethyl-hexylamine oxide had a critical micelle concentration of 0.56 mmol·L$^{-1}$ and $\gamma_{cmc}$ of 35 mN·m$^{-1}$. It indicates that 6-dehydroabietylamide-N,N-dimethyl-hexylamine oxide has good surface activity and can be used to stabilize emulsion.

EXAMPLE 15: PREPARATION OF O/W TYPE GEL EMULSION

An amount of 6-dehydroabietylamide amine oxide was added to a 22 mm (d)×52 mm (h) glass vial with a total volume of 10 mL. After adding a certain amount of deionized water, the vial was heated in a water bath at 50° C. until the 6-dehydroabietylamide amine oxide was completely dissolved to obtain a transparent solution. Different volumes of oil were added to the 6-dehydroabietylamide amine oxide solution (the volume ratios of 6-dehydroabietylamide amine oxide solution to oil were 1:9, 2:8, 3:7, 4:6, 5:5, 6:4, 7:3, 8:2, and 9:1, and total volume was 4 mL), then the mixture was emulsified at 11,000 r/min using an ultraturrax homogenizer (IKA T18 basic, S18N-10G head) for 2 min. The emulsion was allowed to stand and cool at a low temperature to form a white gel emulsion.

Figure 13:
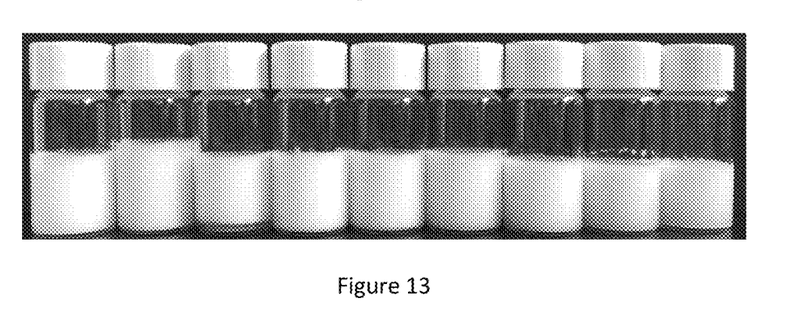
FIG. 13 is a photograph of the appearance of a dodecane/hydrogel emulsion stabilized by 20 mmol·L$^{-1}$ 6-dehydroabietylamide amine oxide at different oil-water ratios (the volume ratio of dodecane/water from left to right is 9:1, 8:2, 7:3, 6:4, 5:5, 4:6, 3:7, 2:8, 1:9).

It can be seen from the photograph of a dodecane/hydrogel emulsion stabilized by 20 mmol·L$^{-1}$ 6-dehydroabietylamide amine oxide at different oil-water ratios in FIG. 13 that the volume fraction of the oil phase was in the range of 10% to 90%, a stable gel emulsion can be formed, and no phase separation occurs.

EXAMPLE 16

The dynamic rheological behavior of the system was determined by a rheometer (Discovery DHR-2, TA). The cone (ETC) used in the test had a cone angle of 2° and a diameter of 40 mm. The distance between the cone and the plate was 48 μm and the temperature was 25° C. First, the elastic modulus (G') and the viscous modulus (G") of the sample as a function of stress (0.1-1000 Pa) were determined to ensure that the subsequent tests for each sample were in the linear viscoelastic region. The stress of 0.8 Pa was selected, the sample was scanned at various frequencies (0.1 to 100 rad/s), and the values of G' and G" as a function of frequency were recorded.

Figure 14:
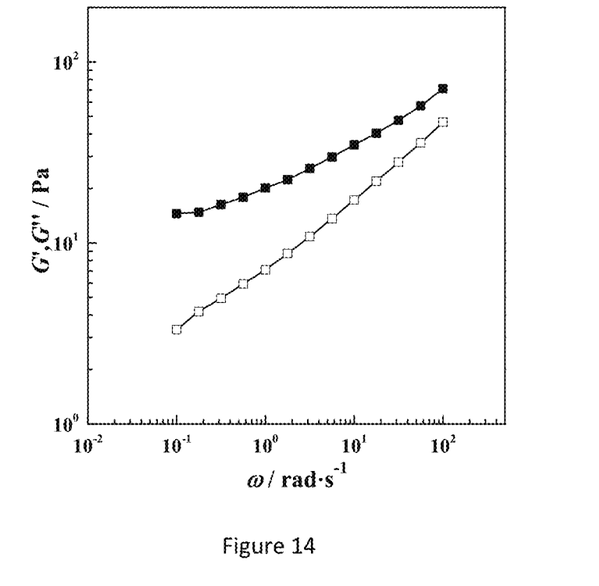
FIG. 14 is a dynamic shear diagram of a dodecane/water ($V_{water}$:$V_{oil}$=1:1) gel emulsion stabilized by 20 mmol·L$^{-1}$ 6-dehydroabietylamide amine oxide (G is the storage modulus with a solid symbol; G" is the loss modulus with a hollow symbol).

It can be seen from the curve of the storage modulus G'and the loss modulus G" of the gel formed by 20 mmol·L$^{-1}$ 6-dehydroabietylamide amine oxide and the dodecane/water ($V_{water}:V_{oil}$=1:1) gel emulsion stabilized by 20 mmol·L$^{-1}$ 6-dehydroabietylamide amine oxide as a function of shear frequency in FIG. 14 that within the frequency range of 0.01-100 rad·s$^{-1}$, the elastic modulus of the corresponding gel emulsion was 67 Pa-14 Pa, and the viscous modulus of the corresponding gel emulsion was 45 Pa-3 Pa. The elastic modulus of the dodecane/water gel emulsion stabilized by 6-dehydroabietylamide amine oxide was always greater than the viscous modulus, indicating the elastic behavior of the gel emulsions.

EXAMPLE 17

Figure 15:
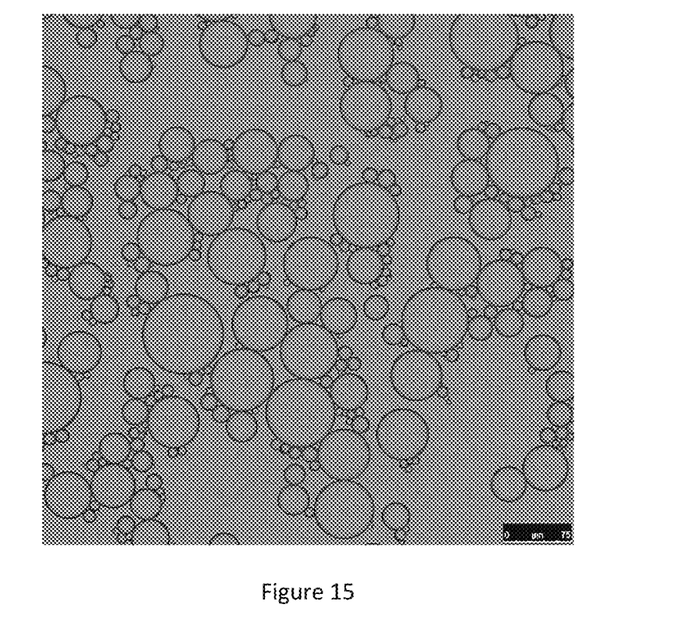
FIG. 15 is a laser confocal micrograph of a dodecane/water ($V_{water}$:$V_{oil}$=8:2) gel emulsion stabilized by 20 mmol·L$^{-1}$ 6-dehydroabietylamide amine oxide.
Figure 16:
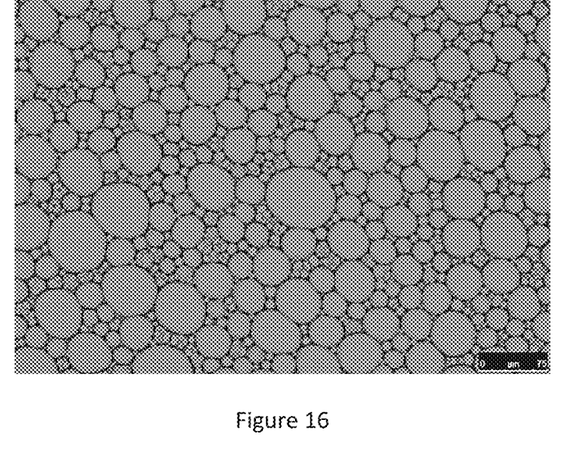
FIG. 16 a laser confocal micrograph of a dodecane/water ($V_{water}$:$V_{oil}$=2:8) gel emulsion stabilized by 20 mmol·L$^{-1}$ 6-dehydroabietylamide amine oxide.

The droplets of the gel emulsion were observed using a TCS SP8 laser confocal microscope from Leica, Germany. A gel emulsion was prepared by adding 1×10$^{-3}$ mol·L$^{-1}$ rhodamine B as an indicator to an aqueous solution of a certain amount of 6-dehydroabietylamide amine oxide. It can be seen from the laser confocal scanning micrograph of a dodecane/water ($V_{water}:V_{oil}$=8:2) gel emulsion stabilized by 20 mmol·L$^{-1}$ 6-dehydroabietylamide amine oxide in FIG. 15 that when the volume fraction of the disperse phase was less than 74%, the droplets of the gel emulsion were regularly spherical. It can be seen from the laser confocal micrograph of a dodecane/water ($V_{water}:V_{oil}$=2:8) gel emulsion stabilized by 20 mmol·L$^{-1}$ 6-dehydroabietylamide amine oxide in FIG. 16 that when the volume fraction of the disperse phase was greater than 74%, the high density extrusion between the droplets caused the emulsion to lose fluidity, and thus the emulsion droplets were polyhedral. When the volume fraction of the dispersed phase was less than 74%, the 6-dehydroabiantylamide amine oxide self-assembled in the continuous phase forms a three-dimensional network structure, preventing the coalescence of the droplets and forming a gel emulsion.

EXAMPLE 18: APPLICATION IN OIL TRANSPORTATION 6-dehydroabiantylamide-N,N-dimethyl-hexylamine oxide as a stabilizer was added to the oil to obtain a solid or semi-solid oil, which reduces the occurrence of oil spillage in the storage container or oil tanks so as to facilitate transport.

After transportation, external stimulation can be performed to demulsify the mixture as required.

The external stimulus can be the addition of an external chemical, such as an alcohol including methanol or ethanol, which destroys the gel structure of the 6-dehydroabietylamide-N,N-dimethyl-hexylamine oxide in the continuous phase. At the same time, the addition of alcohol reduces the stability of the adsorption film formed by the 6-dehydroabietylamide-N,N-dimethyl-hexylamine oxide molecule at the oil-water interface and the water polarity, which leads to the demulsification of the emulsion.

The external stimulus can also be heating. For example, when the gel emulsion was heated to above 40° C., the gel structure of the continuous phase was broken, so that the gel emulsion became a common emulsion. The heating can also increase the Brownian motion of the liquid droplets, causing flocculation and coalescence, which leads to the demulsification of the gel emulsion.

EXAMPLE 19: APPLICATION IN THE PREPARATION OF POROUS MATERIALS

The surface hydrophilic porous material prepared by taking O/W type gel emulsion as a template have good biocompatibility and have potential application value in tissue engineering scaffolds.

6-dehydroabietylamide-N,N-dimethyl-hexylamine oxide was added to deionized water and heated for being completely dissolved. N,N'-methylenebisacrylamide as cross-linking agent and ammonium persulfate and 2-hydroxyethyl methacrylate as initiators were dissolved in the above 6-dehydroabietylamide-N,N-dimethyl-hexylamine oxide solution, after uniformly mixing, dodecane was added, and then the mixture was emulsified at 11,000 r/min using an ultraturrax homogenizer (IKA T18 basic, S18N-10G head) for 2 min to form an O/W emulsion. N,N,N,N-tetramethylethylenediamine as reducing agent was then added to the emulsion. After stirring at 11,000 r/min for 30 s, the emulsion was transferred to a mold (polyethylene container) and cooled to form a gel emulsion, which was incubated at room temperature for 1 h. The obtained solid was immersed in propanol for 24 h and dried under vacuum at 60° C. to obtain a polymer porous material.

Since the oil-water volume ratio of the gel emulsion stabilized by 6-dehydroabietylamide-N,N-dimethyl-hexylamine oxide can be arbitrarily regulated, the porous material prepared by taking the gel emulsion stabilized by 6-dehydroabietylamide-N,N-dimethyl-hexylamine oxide as a template can be arbitrarily adjusted in pore size and distribution.

EXAMPLE 20: GEL EMULSION STABILITY TEST

To the 0.22% solution of 6-dehydroabietylamide amine oxide, different volumes of oil were added (the volume ratios of 6-dehydroabietylamide amine oxide solution to oil were 0.2:9.8, 3:7, 5:5,7:3, and 9.9: 0.1, and total volume was 4 mL), and then the mixture was emulsified at 11,000 r/min using an ultraturrax homogenizer (IKA T18 basic, S18N-10G head) for 2 min. The emulsion was allowed to stand and cool at a low temperature to form a white gel emulsion.

The prepared gel emulsion was placed in a 20° C. incubator, and the stability of the gel emulsion was observed. The results were shown in Table 1 below. When the concentration of 6-dehydroabietylamide-N,N-dimethyl-hexylamine oxide as stabilizer was 0.22% of the mass of the continuous phase, and the volume fraction of the disperse phase was in the range of 1%-98%, a gel emulsion was formed. After placing for one year, the gel emulsion did not undergo demulsification and showed high stability. The higher the stabilizer content, the more stable the gel emulsion formed. Therefore, when the concentration of 6-dehydroabietylamide-N,N-dimethyl-hexylamine oxide as stabilizer ranged from 0.22% to 80% of the mass of the continuous phase, and the volume fraction of the disperse phase ranged from 1% to 98%, the gel emulsion as formed showed a high stability.

TABLE 1

Stability of the gel emulsion stabilized by 0.22% 6-dehydroabietylamide-N,N-dimethyl-hexylamine oxide

| Volume fraction of the continuous phase (%) | Volume fraction of the disperse phase (%) | Stability |
|---|---|---|
| 0.2 | 9.8 | No demulsification occurs after incubation for one year. |
| 3 | 7 | No demulsification occurs after incubation for one year. |
| 5 | 5 | No demulsification occurs after incubation for one year. |
| 7 | 3 | No demulsification occurs after incubation for one year. |
| 9.9 | 0.1 | No demulsification occurs after incubation for one year. |

What is claimed is:

1. A compound, wherein the compound is a 6-dehydroabietylamide-N,N-dimethyl-hexylamine oxide having formula (1):

Formula (1)

2. A method of preparing the compound according to claim 1, wherein the method is as follows:

3. A supramolecular hydrogel comprising the compound according to claim 1, wherein the compound is a gelling factor for forming the supramolecular hydrogel.

4. The supramolecular hydrogel according to claim 3, wherein a concentration of the compound in the supramolecular hydrogel ranges from 3 mmol·L$^{-1}$ to 1,000 mmol·L$^{-1}$.

5. A sustained-release material comprising the compound according to claim 1, and a sustained-release substance.

6. A pharmaceutical wound dressing comprising a hydrogel, wherein the hydrogel comprises the compound according to claim 1 and an inflammatory or anti-bacterial ingredient, wherein the compound is a gelling factor for forming the hydrogel.

7. A water-soil moisturizing agent comprising the compound according to claim 1.

8. A hydrogel mask comprising a hydrogel, wherein the hydrogel comprises the compound according to claim 1, wherein the compound is a gel skeleton for forming the hydrogel.

9. The hydrogel mask according to claim 8, further comprising one or more of collagen, hyaluronic acid, arbutin and nicotinamide injected into the hydrogel mask.

10. A cell culture scaffold prepared by using the compound according to claim 1, wherein the cell culture scaffold is prepared by the following steps: forming a hydrogel by using the compound as a gel skeleton and providing a three-dimensional environment for cell growth.

11. An O/W type gel emulsion prepared by using the compound according to claim 1, wherein a stabilizer of the O/W type gel emulsion is prepared from the compound.

12. The O/W type gel emulsion according to claim 11, wherein a concentration of the compound in the gel emulsion ranges from 0.22% to 80% of a mass of a continuous phase, and a volume fraction of a disperse phase ranges from 1% to 98%.

13. A method for oil transportation using the compound according to claim 1, wherein the method comprises adding the compound as a stabilizer to an oil to obtain a solid or semi-solid oil for transport.

14. A method for synthesizing a porous material by using the compound according to claim 1, wherein the method comprises the following steps: adding a crosslinking agent and an initiator to an aqueous phase; preparing an emulsion containing the compound upon heating; adding a reducing agent to the prepared emulsion; after stirring uniformly, transferring the emulsion to a mold, cooling down to form a gel emulsion and curing; and washing the cured monolith to remove the gel emulsion and then drying.

15. A functional ingredient delivery system based on the compound according to claim 1, wherein the functional ingredient delivery system comprises an O/W type gel emulsion prepared by using the compound, and the functional ingredient is embedded in the gel emulsion; and a functional factor includes: probiotics, flavor substances, nutrients or drugs.

* * * * *